United States Patent [19]

Tejfalussy et al.

[11] 4,155,814

[45] May 22, 1979

[54] METHOD AND APPARATUS FOR GALVANOSTATIC AND POTENTIOSTATIC ELECTROCHEMICAL INVESTIGATION OF THE RATE OF CORROSION PROCESSES

[75] Inventors: Andras Tejfalussy; Dezso Ronay, both of Budapest, Hungary

[73] Assignee: Csepel Muvek Femmuve, Budapest, Hungary

[21] Appl. No.: 856,183

[22] Filed: Nov. 30, 1977

[51] Int. Cl.$^2$ .................. G01N 27/46; G01N 27/30
[52] U.S. Cl. .............................. 204/1 T; 204/195 C
[58] Field of Search ............ 204/1 C, 195 C; 324/29, 324/71 R

[56] References Cited

U.S. PATENT DOCUMENTS 2,947,679  8/1960  Schaschl et al. ............... 204/195 C
3,486,996  12/1969  Annand ........................... 204/195 C
3,504,323  3/1970  Meany, Jr. ........................... 338/13

Primary Examiner—Aaron Weisstuch

[57] ABSTRACT

A method for galvanostatic and potentiostatic electrochemical measurement of the rate of corrosion of an object is described wherein a working electrode, counter-electrode and reference electrode are immersed in an electrolyte and the electromotive force appearing on the cell formed by the working electrode and counter-electrode is measured and related to the reference electrode and the corrosion rate of the object is derived therefrom, the object measured being utilized as a plurality of working electrodes utilized in combination with a plurality of reference electrodes. An apparatus for performing the measurements as above described is also disclosed.

10 Claims, 5 Drawing Figures

METHOD AND APPARATUS FOR GALVANOSTATIC AND POTENTIOSTATIC ELECTROCHEMICAL INVESTIGATION OF THE RATE OF CORROSION PROCESSES

This invention relates to a method enabling the quick corrosion investigation of metallic substances by galvanostatic and potentiostatic electrochemical measurements. Utilizing the method according to the invention, the rate of corrosion processes can be determined and data can be obtained regarding the optimum selection of means for preventing corrosion. The invention relates, furthermore, to an apparatus for the measurement of corrosion resistance of any metal and alloy in the desired environment, either in the form of raw material or as a ready-made shaped article.

According to the techniques applied so far, the corrosion resistance of metallic substances and the rate of corrosion are measured by destructive sampling in electrolytes with pre-determined parameters. In this instance, a sample of the metal or alloy to be examined, generally smaller in volume than 1 cm$^3$, is cut from the metallurgical raw material or a device and is used as the test or "working" electrode. In these measurements sampling has a decisive role. Generally no exact parameters are considered when sampling, thus the sample taken cannot properly represent the material and status of the whole structure. This technique of sampling is based on the assumption that the substance to be examined is completely homogeneous, and the results of the measurements performed under such conditions are regarded as exact data. The accuracy of the measurements is generally considered as a proof of reproducibility.

This concept is, however, basically erroneous and inconsistent. The sample, inhomogeneous by nature, can never represent either the total process or the corrosion characteristics of the structure as a whole in the homogeneous medium. Based on the recent level of scientific and technical knowledge, the method of recording polargraphic curves no more be regarded as appropriate, apart from certain examinations of theoretical value. According to past experiences, the conventional potentiostatic and galvanostatic measurements are useful tools in solving certain theoretical problems, however, the results of such measurements cannot be accepted for the real inhomogeneous environment. It is generally acknowledged that homogeneous conditions do not and cannot prevail under real plant circumstances. In reality, interactions and coefficients of multiple parameters must be taken into account, thus the determination of the properties based on the examination of a sample being considered as a fraction of the total substance is impossible and leads to uncertain results.

No doubt, polarization curves and the apparatuses for recording the same are of great significance. They can be applied for the determination of, e.g., the relative activities of corrosion inhibitors strictly under the same conditions, the passivation ability of a metal or alloy sample in the selected homogeneous system, etc. All of these examinations are, however, extremely lengthy and of extremely low effectiveness and practical value, since a new sample and a new measurement are required when even one of the parameters changes.

As is known, the method of gradient ranging, described first in the Hungarian Pat. No. 163,839, provides technical conditions for the optimization of the inherent changes in metals which facilitate the selection of the location of sampling. This method does not give a directive, however, for the surface electrochemical processes, and does not elucidate the connection between the surface processes and the inner structure. Corrosion processes are, however, surface processes, thus their investigation cannot be solved by adaptation of the above known method.

The object of the present invention is to provide a method for galvanostatic and potentiostatic electrochemical investigation of the rate of corrosion processes, wherein the working-electrode, counter-electrode and reference electrode are immersed in an electrolyte and the electromotive force arising from the cell formed by said working electrode and said counter-electrode is related to said reference electrode. The method of the invention is characterized in that the measurement is carried out as non-destructive testing on the device to be examined, wherein inhomogeneous corrosion conditions are provided for by an electrode system consisting of a number of working electrodes as well as counter-electrodes and reference electrodes, different areas of the device to be tested being used as working electrodes. During the test a spatial combination of at least two corrosion effects is formed, the corrosion behaviour of the surface is registered and evaluated as a function of the inhomogeneities of the corrosion effects and the time, either simultaneously or in one and the same measuring cycle.

Furthermore, the invention relates to an apparatus for performing the above process. The apparatus according to the invention is characterized in that it comprises a solid, pasty or liquid electrolyte, an electrode system consisting of working-, counter- and reference electrodes, wherein different areas of the device to be examined are applied as working electrodes, and a potentiostatic and/or galvanostatic circuit including said electrode system.

The process and apparatus according to the invention offer more possibilities than the prior art. First, the data can be recorded simultaneously in more dimensions than is possible by the known means. Furthermore, the real conditions of multiple parameters are inhomogenized by the novel technique and apparatus to such an approximation until the main phenomenon remains detectable. Using the method and apparatus according to the invention there are recorded simultaneously, besides the environmental parameters (temperature, concentration of the electrolyte, composition of the substance, flow characteristics, etc.) the data of n points appropriately located on the surface or space to be examined, instead of the data of one point, and the changes appearing at these n points characteristic of the electrochemical system are followed as a function of time.

The cell used to perform the above measurement is constructed according to the basic principles of known potentiostatic and galvanostatic techniques to measure the current and potential conditions of the metal surface, characteristic of the corrosion processes proceeding thereon, as a function of the time. In this instance, however, the data set obtained in the measurement is not the picture of a randomly selected point related to homogeneous conditions and thus being strongly idealised, but it is a band-like data set of a real multiparameter system. The signals taken at point n of the construction, appearing at controlled intervals, are led to inlet channel n of a specific electronic device, either a potentiostat or a galvanostat, and the output signal of said potentiostat or galvanostat is fed into a data recording and processing unit. The data processing unit determines the features of the corrosion process and also gives the projected rate of corrosion. This could not be aforeseen according to the knowledge of the state of prior art.

The method and apparatus according to the invention can be applied under laboratory conditions and to examine plant installations. Thus, the electrochemical corrosion processes occurring on the metal surfaces of operating plant equipment, reactors, containers, or other structures can be effectively monitored. When the measurements are repeated at pre-determined intervals, depending on the function of the installation, at the same locations, the corrosion deformations of the structural material can be followed up as a function of the time. The knowledge of the actual corrosion state of an installation and its change as a function of the time is extremely important with respect to the problems of operation, life span and maintenance.

Further details of the invention will be described with reference to the accompanying drawings. In the drawings.

Figure 1:
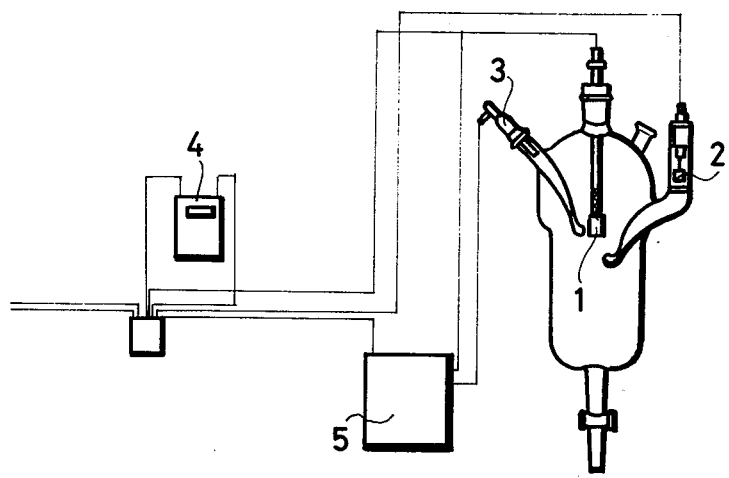
FIG. 1 is a schematic of a conventional potentiostatic measurement.
Figure 2:
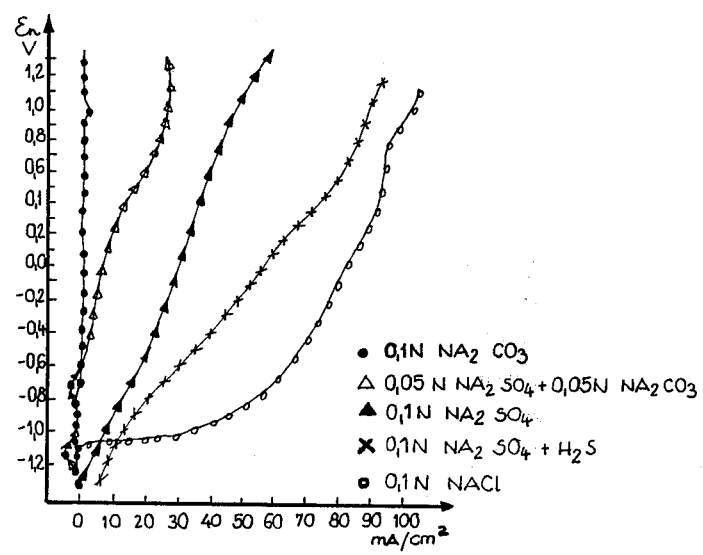
FIG. 2 shows polarization curves obtained by a conventional measurement of a low alloyed steel 17 Mn 4 (according to DIN 17155)

The method according to the invention is illustrated in connection with a conventional potentiostatic measurement, with reference to FIG. 1. As shown in the figure, working electrode 1 to be examined, platinum counter-electrode 2 and reference electrode 3 (calomel) are immersed in an electrolyte of known composition filling the glass container. The electromotive force arising from the cell formed by electrodes 1 and 2 is measured, and it is related to the reference potential (calomel). At the initial stage of the measurement the system has a characteristic rest potential (or corrosion potential). The terminals of the electrodes are connected to potentiostat 4, and polarization is provided by shifting the potential to negative or to positive values with respect to the rest potential. Then, after a certain period (generally 1 to 5 minutes), the system reaches a new rest or equilibrium potential. The latter potential differs, however, from the first one, depending on the direction of the polarization. The current intensity associated with this change in rest potential is detected by electronic unit 5. The characteristics of the electrode are examined using a polarization shift of 10 to 50 mV/1 to 5 minutes. Apparently, when a large installation is under examination, the samples removed from discrete points cannot give a proper indication of the corrosion rate of the installation as a whole. The curves shown in FIG. 2 are the polarization curves obtained using a conventional measurement. All of the curves are obtained by use of separate electrodes. Thus the reproducibility of the measurement is questionable and the measurement is a lengthy procedure.

Figure 3:
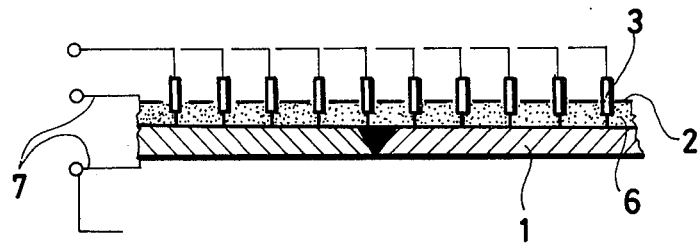
FIG. 3 shows the examination of a container wall.

The method according to the invention disregards the most of the conventional concepts and preserves only the basic principles of the electrode arrangement. According to the invention, not a single separate working electrode and a single reference electrode are utilized, but n reference electrodes are connected to an extended working electrode. The working electrode is, in fact, the wall or other part of the operating installation (see FIG. 3). Thus, there is no need of preparing the working electrode 1 by destruction of said wall or other part; it is sufficient to prepare it by cleaning the appropriate areas of the surface or the entire surface itself. The measurement is performed by using a pasty electrolyte 6 (admixed with gelatine or another appropriate substance), and the platinum wire 2 serving as counterelectrode 2, as well as the capillaries of the calomel reference electrodes 3 are placed in this paste. Using this assembly, one can perform measurements simultaneously at n points, wherein n is equal to the number of the reference electrodes. Output terminals 7 are coupled to a potentiostat or galvanostat having n channels. By this method the inhomogenity of the measuring system is increased intentionally, but only to such an extent that the changes in current intensity and voltage as a function of time are still easily detectable and registrable. The points of measurement may be as close to one another as one cm; no particular difference can be attained with measurements which use smaller distances between the individual points. The distribution of measuring points is determined preferably by preliminary measurements.

The invention is illustrated in detail with the aid of the following non-limiting examples.

EXAMPLE 1

The industrial installation to be examined is a reactor or container used in the chemical industry, which contains an electrolyte of varying composition and corrosivity. Thus, not only the composition and surface condition of the attacked sheet or welded structure is inhomogeneous, but the corrosive medium is inhomogeneous as well. Consequently, there is an inhomogeneous change in corrosion rate. The measurement is performed at points appropriately selected based upon knowledge of the operation of the installation. The selected points are marked, and the measurement is repeated at regular intervals depending on the corrosion rate (e.g. in every third month, every year, etc.) at the marked points. Using this method, a time-map is obtained which shows the corrosion state of the installation. This time-map enables one to decide where perforation can be expected, where it is necessary to protect the surface, how the protection changes with time, etc. The electrolyte paste and the appropriate electrode system are placed onto the cleaned surface parts, the current-voltage curves are recorded, and the projected rate of corrosion of the structural material is determined from the data obtained. The measurement can be performed on both new and already operating installations. When an operating installation is to be examined, it is preferable to remove the substance stored in it, provided that it disturbs the measurement.

Besides the examination of the inner wall, it is preferred to perform measurements on the outer wall as well, in order to obtain information about the effects of the environment.

EXAMPLE 2

Figure 4:
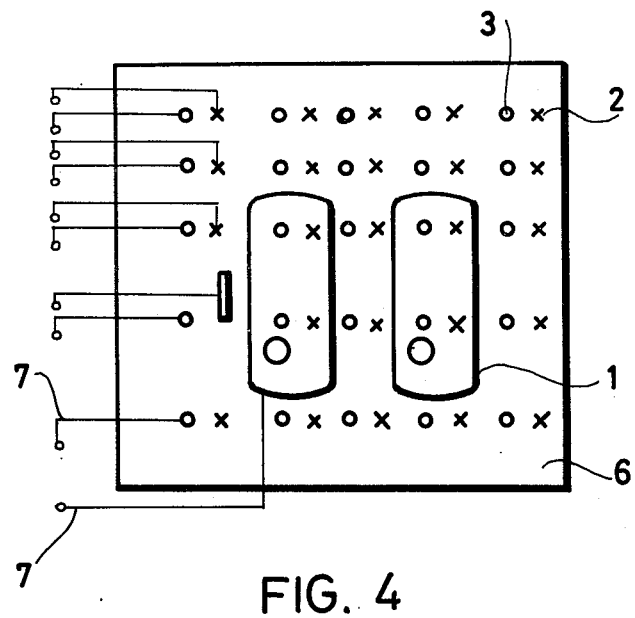
FIG. 4 shows the examination of an underground container park.

The arrangement of an underground container park is shown in FIG. 4. The reference electrodes 3 (Cu/CuSO$_4$) are arranged in a network system on the ground above the container park, in order to determine the corrosion state thereof. In this instance, the soil serves as electrolyte 6. The working electrode 1 is the container itself, whereas the ground plate or the anode of the cathodic protection system may serve as counter-electrode 2. The data recorded at the outputs 7 indicate simultaneously the interactions, the changes of soil resistance, the effects of outer currents and the zones with different corrosivities, and give also information about the state of the insulation. These data are also forwarded to a potentiostat system.

EXAMPLE 3

Figure 5:
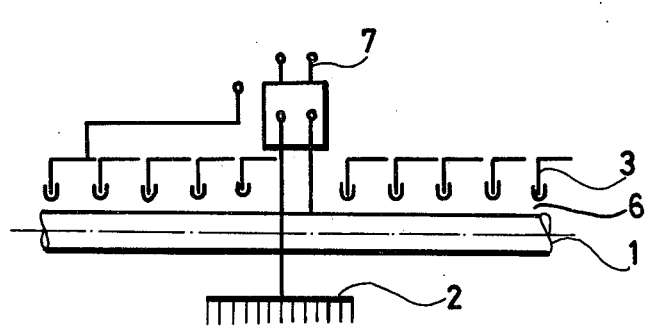
FIG. 5 shows the determination of a pipe system.

The arrangement for determination of the corrosion state or corrosion processes of an underground pipe system is shown in FIG. 5. Cu/CuSO$_4$ reference electrodes 3 are placed in a network system on the ground surface along the trajectory. The working electrode 1 is the pipe, the counter-electrode 2 is the grounded anode, and the electrolyte 6 is the soil. By this measurement the corrosion zones, the defects of insulation and the corrosion state of the pipe system can be determined.

What we claim is:

1. A method for galvanostatic and potentiostatic electrochemical measurement of the rate of corrosion processes, wherein a working electrode, counter-electrode and reference eletrode are immersed in an electrolyte and the electromotive force appearing on the cell formed by said working electrode and said counter-electrode is measured and related to said reference electrode and the corrosion rate derived therefrom, comprising carrying out said measurement as non-destructive testing on the object to be examined, wherein inhomogeneous corrosion conditions are provided for by an electrode system comprising a plurality of working electrodes, at least one counter-electrode and a plurality of reference electrodes, different areas of the object to be examined forming said plurality of working electrodes, and during the test a spatial combination of at least two corrosion effects is formed, the corrosion behavior of the surface is recorded and evaluated as a function of the inhomogeneities of the corrosion effects and the time, either simultaneously or in one and the same measuring cycle.

2. The method as claimed in claim 1, wherein a solid electrolyte is used.

3. The method as claimed in claim 1, wherein a pasty electrolyte is used.

4. The method as claimed in claim 1, wherein a liquid electrolyte is used.

5. The method as claimed in claim 1 which is applied over a long period of time while periodically sampling the test results.

6. The method as claimed in claim 1, wherein the multiple electrode system is sampled by scanning, applying only one pair of said working and reference electrodes at a time.

7. A process as claimed in claim 1, wherein it is applied in a semiautomatic or automatic system for active and passive corrosion inhibiting purposes.

8. An apparatus for measuring the rate of corrosion of an object comprising means for providing an electrolyte, means for supporting a plurality of working electrodes, at least one counter-electrode and a plurality of reference electrodes in said electrolyte, said counter-electrode being in the form of a metal net and the reference electrode being in the form of capillaries forming a structural unit with said metal net, different areas of the object to be examined forming said plurality of working electrodes, and means connected to said electrodes for measuring and recording the corrosion behavior of the surface of said object.

9. An apparatus according to claim 8, wherein potentiostatic measuring means is employed.

10. An apparatus according to claim 8, wherein galvanostatic measuring means is employed.

* * * * *